US010258372B2

(12) United States Patent
Pattison et al.

(10) Patent No.: US 10,258,372 B2
(45) Date of Patent: Apr. 16, 2019

(54) TRANSABDOMINAL GASTRIC SURGERY SYSTEM AND METHOD

(71) Applicant: Endo-Tagss, LLC, Leawood, KS (US)

(72) Inventors: Mary Pattison, Kansas City, MO (US); Charles Phillip Pattison, Kansas City, MO (US); Stephen J. Lowry, Kansas City, MO (US); Mark A. Molos, Kansas City, MO (US)

(73) Assignee: ENDO-TAGSS, LLC, Leawood, KS (US)

( * ) Notice: Subject to any disclaimer, the term of this patent is extended or adjusted under 35 U.S.C. 154(b) by 629 days.

(21) Appl. No.: 14/451,108

(22) Filed: Aug. 4, 2014

(65) Prior Publication Data

US 2015/0038794 A1    Feb. 5, 2015

Related U.S. Application Data

(60) Provisional application No. 61/862,357, filed on Aug. 5, 2013, provisional application No. 61/862,358, filed on Aug. 5, 2013.

(51) Int. Cl.
| | | |
|---|---|---|
| *A61B 17/34* | (2006.01) | |
| *A61B 17/00* | (2006.01) | |
| *A61M 25/02* | (2006.01) | |

(52) U.S. Cl.
CPC ...... *A61B 17/3462* (2013.01); *A61B 17/3415* (2013.01); *A61B 2017/00278* (2013.01);
(Continued)

(58) Field of Classification Search
CPC ........ A61B 17/3423; A61B 2017/3466; A61B 2017/3441; A61B 2017/3427;
(Continued)

(56) References Cited

U.S. PATENT DOCUMENTS

| 4,315,513 A | 2/1982 | Nawash et al. |
|---|---|---|
| 4,356,824 A | 11/1982 | Vasquez |

(Continued)

FOREIGN PATENT DOCUMENTS

| WO | WO2007/136683 | 11/2007 |
|---|---|---|
| WO | WO2010/087690 | 8/2010 |

(Continued)

OTHER PUBLICATIONS

U.S. Appl. No. 14/554,337, filed Nov. 26, 2014.
(Continued)

*Primary Examiner* — David W Bates
(74) *Attorney, Agent, or Firm* — Leydig, Voit & Mayer, Ltd.

(57) ABSTRACT

The present disclosure generally relates to a system and method for providing transabdominal gastric surgical access system for medical, endoscopic, and surgical instruments through a percutaneous surgically constructed opening. More particularly, it concerns a delivery system and a surgery system having structures that includes a cannula working channel, an internal and external anchor system, a cap and insertion tool for creating an opening, to provide gastric access through at least one port for the insertion of instruments for medical/surgical procedures.

11 Claims, 15 Drawing Sheets

(52) U.S. Cl.
CPC . *A61B 2017/349* (2013.01); *A61B 2017/3425* (2013.01); *A61B 2017/3466* (2013.01); *A61B 2017/3482* (2013.01); *A61B 2017/3484* (2013.01); *A61B 2017/3488* (2013.01); *A61B 2017/3492* (2013.01); *A61M 2025/0233* (2013.01)

(58) Field of Classification Search
CPC .... A61B 2017/3482; A61B 2017/3492; A61B 2017/349; A61B 2017/00637; A61B 2017/00659
See application file for complete search history.

(56) References Cited

U.S. PATENT DOCUMENTS

| | | | |
|---|---|---|---|
| 4,668,225 A | 5/1987 | Russo et al. | |
| 5,007,900 A | 4/1991 | Picha et al. | |
| 5,071,405 A | 12/1991 | Piontek et al. | |
| 5,112,310 A | 5/1992 | Grobe | |
| 5,147,316 A | 9/1992 | Castillenti | |
| 5,167,627 A | 12/1992 | Clegg et al. | |
| 5,259,399 A | 11/1993 | Brown | |
| 5,391,159 A | 2/1995 | Hirsch et al. | |
| 5,527,280 A | 6/1996 | Goelz | |
| 5,716,347 A | 2/1998 | Gibbs et al. | |
| 5,720,734 A | 2/1998 | Copenhaver et al. | |
| 5,865,816 A | 2/1999 | Quinn | |
| 5,993,473 A | 11/1999 | Chan et al. | |
| 6,030,361 A | 2/2000 | Miyashiro | |
| 6,234,958 B1* | 5/2001 | Snoke | A61B 1/00082 600/106 |
| 6,419,670 B1 | 7/2002 | Dikeman | |
| 6,451,041 B1* | 9/2002 | Moenning | A61B 17/3417 604/164.04 |
| 6,454,785 B2 | 9/2002 | De Hoyos Garza | |
| 6,458,077 B1* | 10/2002 | Boebel | A61B 1/12 600/114 |
| 6,551,270 B1 | 4/2003 | Bimbo et al. | |
| 6,907,992 B2 | 6/2005 | McMichael et al. | |
| 6,910,581 B2 | 6/2005 | McMichael et al. | |
| 7,025,791 B2 | 4/2006 | Levine et al. | |
| 7,122,058 B2 | 10/2006 | Levine et al. | |
| 7,220,284 B2 | 5/2007 | Kagan et al. | |
| 7,267,694 B2 | 9/2007 | Levine et al. | |
| 7,314,489 B2 | 1/2008 | McKenna et al. | |
| 7,316,716 B2 | 1/2008 | Egan | |
| 7,329,285 B2 | 2/2008 | Levine et al. | |
| 7,347,875 B2 | 3/2008 | Levine et al. | |
| 7,476,256 B2 | 1/2009 | Meade et al. | |
| 7,563,254 B2 | 7/2009 | Delegge | |
| 7,582,072 B2 | 9/2009 | McMichael | |
| 7,678,068 B2 | 3/2010 | Levine et al. | |
| 7,682,330 B2 | 3/2010 | Meade et al. | |
| 7,695,446 B2 | 4/2010 | Levine et al. | |
| 7,758,535 B2 | 7/2010 | Levine et al. | |
| 7,766,861 B2 | 8/2010 | Levine et al. | |
| 7,766,973 B2 | 8/2010 | Levine et al. | |
| 7,794,447 B2 | 9/2010 | Dann et al. | |
| 7,806,870 B2 | 10/2010 | Mastri et al. | |
| 7,815,591 B2 | 10/2010 | Levine et al. | |
| 7,819,836 B2 | 10/2010 | Levine et al. | |
| 7,824,368 B2 | 11/2010 | Clem et al. | |
| 7,833,156 B2 | 11/2010 | Williams et al. | |
| 7,833,202 B2 | 11/2010 | Suzuki | |
| 7,837,643 B2 | 11/2010 | Levine et al. | |
| 7,935,073 B2 | 5/2011 | Levine et al. | |
| 7,976,488 B2 | 7/2011 | Levine et al. | |
| 7,981,163 B2 | 7/2011 | Meade et al. | |
| 8,057,420 B2 | 11/2011 | Meade et al. | |
| 8,096,966 B2 | 1/2012 | Levine et al. | |
| 8,097,000 B2 | 1/2012 | Albrecht | |
| 8,109,910 B2 | 2/2012 | Zastawny et al. | |
| 8,109,943 B2 | 2/2012 | Boraiah et al. | |
| 8,137,301 B2 | 3/2012 | Levine et al. | |
| 8,147,454 B2 | 4/2012 | Watanabe et al. | |
| 8,147,561 B2 | 4/2012 | Binmoeller | |
| 8,162,871 B2 | 4/2012 | Levine et al. | |
| 8,182,459 B2 | 5/2012 | Dann et al. | |
| 8,206,456 B2 | 6/2012 | Stack et al. | |
| 8,211,186 B2 | 7/2012 | Belhe et al. | |
| 8,246,617 B2 | 8/2012 | Welt et al. | |
| 8,303,669 B2 | 11/2012 | Meade et al. | |
| 8,430,811 B2 | 4/2013 | Hess et al. | |
| 9,877,744 B2* | 1/2018 | Cooper | A61B 17/3421 |
| 2002/0042607 A1 | 4/2002 | Palmer et al. | |
| 2002/0055757 A1 | 5/2002 | Torre et al. | |
| 2003/0097099 A1 | 5/2003 | Quinn | |
| 2003/0158569 A1 | 8/2003 | Wazne | |
| 2003/0225393 A1 | 12/2003 | McMichael et al. | |
| 2004/0059289 A1 | 3/2004 | Garza | |
| 2005/0049624 A1 | 3/2005 | Francese et al. | |
| 2005/0240279 A1 | 10/2005 | Kagan et al. | |
| 2005/0267415 A1 | 12/2005 | Jacques | |
| 2006/0020241 A1* | 1/2006 | Piskun | A61B 17/3403 604/93.01 |
| 2006/0030872 A1 | 2/2006 | Culbert et al. | |
| 2006/0052752 A1* | 3/2006 | McMichael | A61J 15/0034 604/175 |
| 2006/0247516 A1* | 11/2006 | Hess | A61B 1/32 600/426 |
| 2007/0123840 A1 | 5/2007 | Cox | |
| 2007/0156165 A1 | 7/2007 | Chang et al. | |
| 2007/0225728 A1 | 9/2007 | Stefanchik et al. | |
| 2007/0255257 A1 | 11/2007 | Willis et al. | |
| 2008/0249474 A1 | 10/2008 | Baker | |
| 2008/0255519 A1* | 10/2008 | Piskun | A61B 1/32 604/174 |
| 2009/0036745 A1* | 2/2009 | Bonadio | A61B 17/3423 600/208 |
| 2009/0204067 A1* | 8/2009 | Abu-Halawa | A61B 17/3415 604/96.01 |
| 2009/0299486 A1 | 12/2009 | Shohat et al. | |
| 2010/0081875 A1 | 4/2010 | Fowler et al. | |
| 2010/0081880 A1* | 4/2010 | Widenhouse | A61B 17/3462 600/201 |
| 2010/0081883 A1 | 4/2010 | Murray et al. | |
| 2010/0152764 A1 | 6/2010 | Merkle | |
| 2010/0204707 A1* | 8/2010 | Tanaka | A61M 1/04 606/108 |
| 2010/0249525 A1* | 9/2010 | Shelton, IV | A61B 17/3423 600/208 |
| 2010/0249526 A1* | 9/2010 | Shelton, IV | A61B 17/0293 600/208 |
| 2010/0249822 A1 | 9/2010 | Nihalani | |
| 2010/0280368 A1 | 11/2010 | Can et al. | |
| 2010/0312047 A1 | 12/2010 | Forsell | |
| 2010/0324375 A1 | 12/2010 | Piskun | |
| 2010/0331756 A1 | 12/2010 | Meade et al. | |
| 2011/0028793 A1 | 2/2011 | Martin et al. | |
| 2011/0046537 A1 | 2/2011 | Errico et al. | |
| 2011/0082442 A1 | 4/2011 | Solovay et al. | |
| 2011/0106273 A1 | 5/2011 | Belhe et al. | |
| 2011/0160539 A1 | 6/2011 | Robertson | |
| 2011/0245751 A1 | 10/2011 | Hoffmann | |
| 2011/0257580 A1 | 10/2011 | Meade et al. | |
| 2011/0276091 A1 | 11/2011 | Melanson et al. | |
| 2011/0301523 A1 | 12/2011 | Levine et al. | |
| 2012/0029413 A1 | 2/2012 | Meade et al. | |
| 2012/0078174 A1 | 3/2012 | Tai et al. | |
| 2012/0095495 A1 | 4/2012 | Babkes et al. | |
| 2012/0116362 A1 | 5/2012 | Kieturakis | |
| 2012/0132212 A1 | 5/2012 | Nishtala | |
| 2012/0184967 A1 | 7/2012 | Levine et al. | |
| 2012/0203271 A1 | 8/2012 | Larkin et al. | |
| 2012/0215152 A1 | 8/2012 | Levine et al. | |
| 2012/0232339 A1 | 11/2012 | Csiky | |
| 2012/0323081 A1 | 12/2012 | Son | |
| 2013/0012862 A1 | 1/2013 | Meade et al. | |
| 2013/0041231 A1 | 2/2013 | Bonadio et al. | |
| 2013/0041372 A1 | 2/2013 | Welt et al. | |
| 2013/0060091 A1 | 3/2013 | Azarbarzin et al. | |
| 2013/0066304 A1 | 3/2013 | Belson et al. | |

(56) References Cited

U.S. PATENT DOCUMENTS

| | | |
|---|---|---|
| 2013/0102876 A1 | 4/2013 | Limon et al. |
| 2013/0211196 A1 | 8/2013 | Belson et al. |
| 2014/0058362 A1 | 2/2014 | Tycast et al. |
| 2014/0276338 A1 | 9/2014 | Pattison et al. |

FOREIGN PATENT DOCUMENTS

| | | |
|---|---|---|
| WO | WO2011/004335 | 1/2011 |
| WO | WO2011/072096 | 6/2011 |
| WO | WO2015/020977 | 8/2014 |
| WO | WO2014/145799 | 9/2014 |

OTHER PUBLICATIONS

U.S. Appl. No. 14/216,666, filed Mar. 17, 2017, 2014/0276338, Sep. 18, 2014.

U.S. Appl. No. 14/554,677, filed Nov. 26, 2014.

International Search Report and Written Opinion Corresponding to International Application No. PCT/US2014/030625, Completed Aug. 1, 2014.

International Search Report and Written Opinion of the International Searching Authority Corresponding to International Application No. PCT/US2014/049639, Completed Nov. 12, 2014.

International Search Report and Written Opinion of the International Searching Authority Corresponding to International Application No. PCT/US14/67689, Completed Mar. 30, 2015.

International Search Report and Written Opinion of the International Searching Authority Corresponding to International Application No. PCT/US14/67697, Completed Mar. 30, 2015.

Supplementary Partial European Search Report corresponding to European Patent Application No. 14835461.6, dated Mar. 15, 2017.

Supplementary European Search Report corresponding to European Patent Application No. 14835461.6, dated Jun. 16, 2017.

Examination Report corresponding to Australian Patent Application No. 2014306164, dated May 15, 2018.

First Office Action corresponding to Chinese Patent Application No. 2014800549229, including English translation, dated Apr. 28, 2018.

Extended European Search Report corresponding to European Patent Application No. 14907024.5, dated Jun. 14, 2018.

\* cited by examiner

A

B

C

D

E

A

B

C

TRANSABDOMINAL GASTRIC SURGERY SYSTEM AND METHOD

CROSS-REFERENCE TO RELATED APPLICATIONS

This application relates to and claims priority to U.S. Provisional Patent Applications No. 61/862,357 and 61/862,358, which were filed Aug. 5, 2013 and are incorporated herein by reference in their entirety.

FIELD

The present disclosure generally relates to a system and method for providing a transabdominal gastric surgical access system for medical, endoscopic, and surgical instruments through a percutaneous surgically constructed opening. More particularly, it concerns a delivery system and a surgery system having structure for creating and enlarging the opening, and providing gastric access through multiple ports for the insertion of surgical instruments for medical procedures.

BACKGROUND

A variety of surgical treatments have recently become available to address abdominal and pelvic disease including obesity and related disorders. In the medical field many therapeutic upper gastrointestinal (UGI) tract procedures are routinely performed by flexible endoscopy, without creating an external surgical opening. In such procedures an endoscope is introduced via the patient's mouth, through the patient's oropharynx and esophagus into the lumen of the stomach.

The endoscopes used in the industry include a light delivery system for illuminating the interior of an organ and may be used to evaluate the site, an ability to insufflate air into the gastrointestinal lumen, and also have a narrow working channel to allow for easy introduction of instruments in the patient for performing procedures such as obtaining biopsy specimens, cauterization, and polyp removal. Minimally invasive procedures are desired by both the medical personnel and the patient, because of the potential for quicker recovery and reduced surgical complications. However, use of endoscope instruments limits the ease of use due to the small diameter of the working channel which limits the size and type of instruments that may be used as well as the procedures that can be performed.

In addition to the small diameter of the working channel, all instruments by the very nature of the flexible endoscopy platform are introduced in a "parallel" relation to each other as well as the endoscope itself which results in an inherently limiting factor for performing advanced endolumenal and extralumenal procedures. This limiting factor prevents the physician in using these instruments in an otherwise standard surgical means, process and technique called triangulation of the instruments. This inability to triangulate instruments limits the types of procedures that can be performed by the current standard flexible endoscopy platform. This includes not only the instruments and devices passed through the working channel or channels of the endoscope but in addition includes any instruments or devices that have previously been developed for attaching themselves to the side or tip of the endoscope. In addition, the efficiency of the available procedures is less than optimal.

Because passage of a flexible endoscope for UGI procedures by its very nature must past through the oropharynx; the size of the oropharynx becomes a limiting factor. Thus, only a single endoscope which can only vary minimally in diameter may be inserted at any one time via the patient's esophagus. These aspects effectively have precluded, or increased the risk of complications from the use of endoscopic introduced instruments to create access via an opening from the lumen of the stomach and/or into the extralumenal space, such as the peritoneal cavity, perform a surgical procedure, withdraw the instrument, and close the opening.

Limitations on general endoscopic procedures have also limited the performance and advancement of endolumenal endoscopic procedures. The use of standard flexible endoscopy has created minimal treatment options or surgical options for evaluation and treatment in the gastrointestinal tract. The current industry has tried unsuccessfully to develop and expand the role of standard flexible endoscopy and the creation of a platform of instruments which could be used to perform advanced intralumenal endoscopic procedures as well as extralumenal procedures. One example has been natural orifice translumenal endoscopic surgery (NOTES). NOTES was developed to expand the role of standard flexible endoscopy and provide a platform and instruments which could be used to perform advanced intralumenal endoscopic procedures as well as extralumenal procedures. The NOTES concept and platform has not been successfully integrated into standard GI endoscopy or surgical procedures due to the bulky instruments which are difficult to pass safely through the oropharynx. The current NOTES devices in the industry have not met the required elements for success in accessing the extralumenal space, performance of the procedure, and closure of the opening.

In addition to the use of an endoscope for minimal invasive surgical procedures, laparoscopic surgery is another option. In laparoscopic surgery multiple small surgical openings are created through the abdominal wall and tissue and a laparoscope is introduced through one of the openings and into the peritoneal cavity. The laparoscope is able by its very nature to examine the outside of the gastrointestinal tract and the solid organs of the abdominal-pelvic cavity and intraperitoneal space. Trocars, hollow tubes with sharp tips, are introduced into the other openings and instruments are introduced into the peritoneal cavity through the trocars to perform surgical operations on the outside of the abdominal organs such as the stomach, small intestine, colon, spleen, gall bladder, pancreas and liver. Access to these organs via laparoscopic surgery is extralumenal, from the peritoneal cavity, rather than endolumenal through the lumens of the gastrointestinal tract. In addition, such current endoscopic and laparoscopic surgical devices and procedures do not have the ability or a device designed and available to provide both external and internal anchors to retain the wall of the stomach in place against the abdominal wall during the procedure for both intraluminal and extralumenal access to provide a safe, stable, and reliable working channel which traverses and stabilizes the abdominal wall and gastric wall between the internal and external anchors. In addition, such current endoscopic and laparoscopic surgical procedures do not have the ability or a device to provide an endoscopically placed trocar or access device to provide the ability for the simultaneous access to the GI tract and peritoneal cavity for both intralumenal and extralumenal procedures.

It is also known in the industry to use percutaneous endoscopic gastrostomy (PEG) tubes for feeding and delivery of nutrients to a patient. A PEG is put in place by insertion through a surgical opening or stoma into the stomach of a patient to allow for fluid passage. The PEG feeding tubes must be soft and flexible and are generally formed of silicone or the like, which could be easily punctured by surgical instruments. The design is important for the desired purpose, but lacks the ability for insertion of surgical or medical devices or to perform surgical procedures. Further the similar limiting factors found in endoscopic procedures are also found with the PEG because of the size and weakness of material required for the PEG.

There is a need for a trans-abdominal gastric surgery system that provides new and unique device or system and introducer device to create a minimally invasive single port access with a working channel for the introduction of instruments used to access the gastric lumen, peritoneal space, or retroperitoneal space. The system further requires an anchoring system with internal and external anchors to stabilize the gastric and abdominal wall while creating a luminal access. A system is also desired that is easier to use by a medical professional by providing "triangulation" of both laparoscopic and endoscopic instruments and minimizes the pain and post-op recovery by a patient. A system that provides for a sealed access to simultaneously allow intraluminal surgical access to the stomach lumen and through the lumen of the upper GI tract or also out into the peritoneal cavity or retroperitoneal space, that permits the passage, use, and rotation of surgical instruments through a single cannula having multiple ports or multiple cannulas that permit "triangulation" necessary for accurate performance of delicate procedures. The system further desired includes the ability for air or $CO_2$ insufflation to control and monitor the pressure during the procedure. Further, a system is desired that allows for adjustment of the length and radial diameter of the cannula, that further provides an adjustable internal fixation device through which multiple instruments may pass, and can remain in a patient's body for the duration of the procedure and once removed can provide an easy and efficient method of closure of the transabdominal access following the removal of medical instruments.

Further, there is a need for an introducer and device that allows for performing intralumenal and extralumenal procedures that can further include standard endoscopic and laparoscopic platforms, but overcomes the limitations currently found due to size constraints and lack of triangulation.

SUMMARY

The present disclosure provides a greatly improved surgical system for providing transabdominal access into the gastric lumen, UGI tract lumen, and peritoneal or retroperitoneal spaces for introducing medical instruments and devices and performing medical procedures. The system allows for stand-alone use or for the integration with standard flexible endoscopy and laparoscopy procedures for improved and increased access to patients for advanced endolumenal and extralumenal procedures. The implementation and use of the system will create a platform device to increase the safety and decrease the time associated with typical prolonged surgical procedures and the associated recovery which is desired by the healthcare provider and patient.

The system includes a cannula including an inner end, an opposed outer end, and a sidewall between the ends, the sidewall circumscribing a lumen. An internal anchor is connected with the cannula adjacent to the inner end and includes a central aperture for receiving the cannula there through. The internal anchor is actuable from a non-deployed position to a deployed position disposed to contact the inner wall of the stomach.

The system also includes at least one external anchor or anchor disc for securing an outer portion of the cannula in place of the surgical opening adjacent to the external surface. The external anchor is configured with a central aperture sized for receiving the cannula there through. At least one of the discs also includes a plurality of access holes configured to permit the introduction of surgical instruments or sutures through the access holes and the lumen and into the stomach of the patient to perform closure of the site. Each selectable disc also includes structure disposed to connect the disc to the cannula sidewall or end.

The system further includes a cap for connection to the cannula and optionally the anchor disc. The cap can further include a memory sealant configured to allow for an airtight passage when connected in place to the cannula. The cap can further include multiple access ports for use with the cannula allowing for increased flexibility and introduction and placement of medical and surgical instruments into the interior of the stomach at various angles to aide in triangulation. The cap may further include a port for insufflation of a gas to control and monitor pressure during the procedure.

The external anchor disc is configured with needle catheter guides to allow placement of sutures for closure of the surgical opening prior to the beginning of any anticipated surgical procedures. In addition the external anchor disc provides stabilization of the surgical system.

Each of the discs may include a connecting structure disposed to adjustably connect the disc to the adjacent discs. The anchor discs and the internal anchor may also be disposed to cooperatively and adjustably fasten the wall of the stomach to the abdominal wall of the patient, without damaging the tissue of the patient.

In one aspect, the cannula includes a plurality of telescoping cannula sections. Each section is sized and configured for telescoping reception of a portion of the section within a portion of the lumen of an adjacent section, so that the overall length of the cannula may be reduced during insertion. The sections are removably connected to the adjacent sections to permit removal of one or more sections from the end of the cannula. Each cannula section may also be constructed of a material having different physical properties.

In another aspect, the cannula is constructed in an axially folded or compressed manner that can be later expanded to permit the introduction of larger medical instruments and devices.

The system is further configured to allow for the simultaneous performance and use with standard endoscopic and laparoscopic platforms, instruments and devices to allow for introduction of such devices into the gastric lumen, peritoneal, and/or retroperitoneal spaces. In addition the configuration of the system allows for the additional use of standard trans-oral flexible endoscopy with the other surgical devices to allow the performance of advanced intralumenal or extra luminal procedure.

The system includes an introducer dilator-type placement tool that is tapered at its proximal end and increases in size and diameter to its distal end having a generally conical shape with a central lumen equipped with a generally cylindrical core element. A guide wire extends through a central lumen of the tool. The introducer placement tool has a unique and specially sized and designed recessed area at its more proximal end. This recessed area is sized to allow for pre-loaded placement of the cannula so it sits flush with the introducer tool. The proximal aspect of the recessed region can be a removable front bumper forming the recessed area.

A method of inserting and using the system for performing transabdominal gastric surgery involves preloading the placement tool with the cannula, using the guide wire to guide insertion of the placement tool through the oropharyngeal cavity of a patient, through the esophagus and into the patient's stomach. The placement tool is used to install the cannula in a retrograde manner, proceeding outwardly from the stomach through the abdominal wall when placing the cannula into the correct position. The guide wire is controlled at the oral pharynx end as well as the external abdominal wall end through-out the placement process. The inner aspect of the cannula or device with the unfolded inner bumper rests removable against the inner gastric wall. The external aspect of the cannula or device is anchored at the abdominal wall by an external disc. This retrograde passage of the pre-loaded introducer containing the device is used to create a surgically constructed opening that extends through the stomach wall and the abdominal wall and out to the surface of the skin. The introducer placement tool dilator is withdrawn, leaving the cannula in place with the inner end positioned adjacent the inner surface of the wall of the stomach and the outer end extending outwardly through the abdominal wall and skin from the stoma. The internal anchor is placed or deployed against the interior surface of the gastric wall to retain the lower end of the device in position at the stomach wall. One or more exterior anchor discs are selected, fastened to each other, installed over the cannula, and fastened in place on the cannula. The cap has an external shell with an inner seal which screws onto the external portion of the cannula. Multiple laparoscopic instruments may then be inserted alone or simultaneously through the cap containing the memory sealant then through the lumen of the cannula into the gastric lumen. If the inner bumper is adjusted to the inner aspect of the abdominal wall then instruments will pass into the cap then through the lumen of the cannula into the peritoneal cavity. An endoscope may also be deployed at the same time through the esophagus and into the stomach and/or the peritoneal cavity.

In another aspect, a similar introducer dilator is used to introduce the device from outside the patient through the stoma, abdominal wall and gastric wall and into the lumen of the stomach.

The method may also include breaking off selected telescoping elements of the cannula to achieve a cannula having a desired length. Where the cannula is of radially compressed construction, the method may include radial expansion of the cannula within the stoma to an expanded configuration, thereby expanding the diameter of the opening to provide an access channel having a diameter sufficient to accommodate a desired number of medical instruments.

Various objects, features and advantages of this disclosure will become apparent from the following detailed description, which, taken in conjunction with the accompanying drawings, which depict, by way of illustration and example, certain embodiments of this system.

The drawings constitute a part of this specification, include various exemplary embodiments of the trans abdominal gastric surgical system, and illustrate various objects and features thereof.

DETAILED DESCRIPTION

Figure 3:
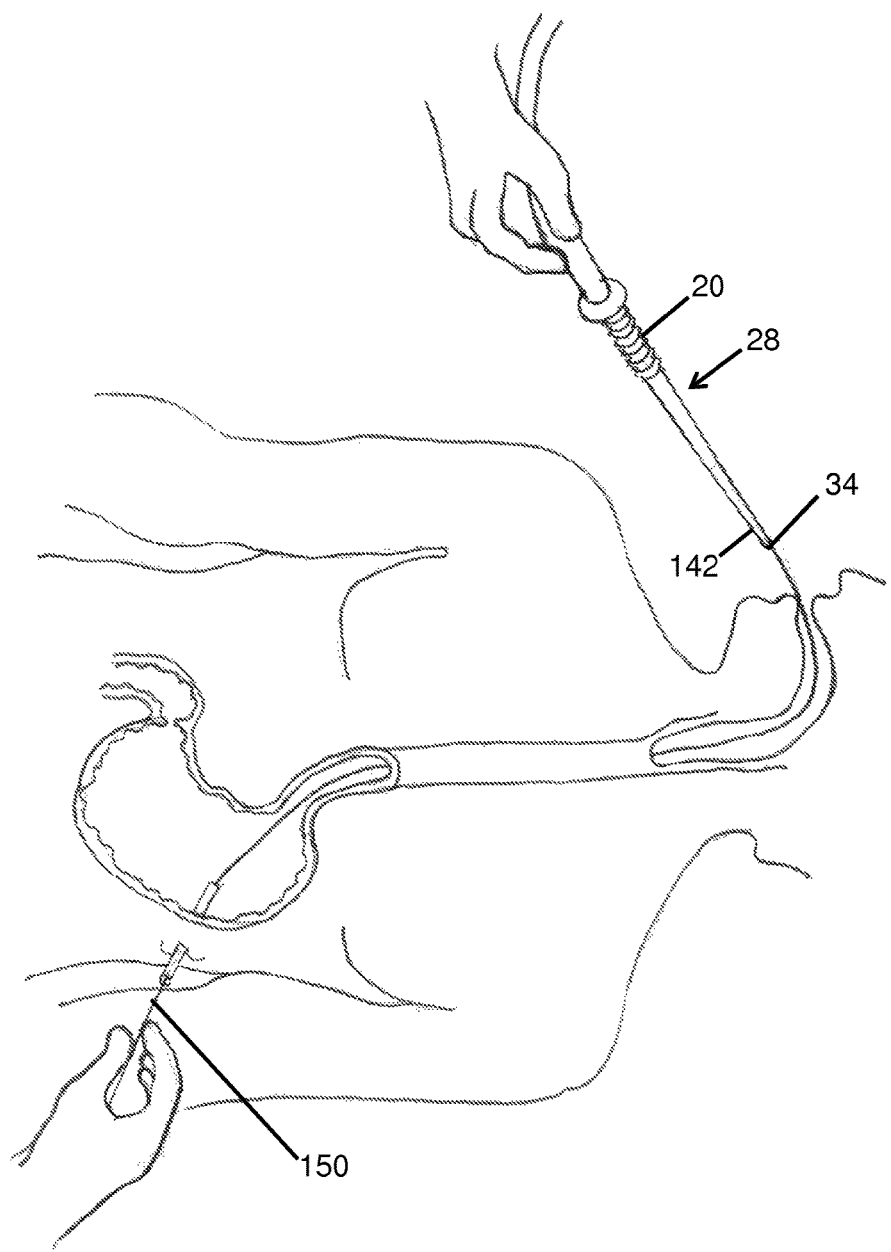
FIG. 3 is a perspective view of the insertion of the surgical device with the introducer device in a cross sectional view of the patient.
Figure 4:
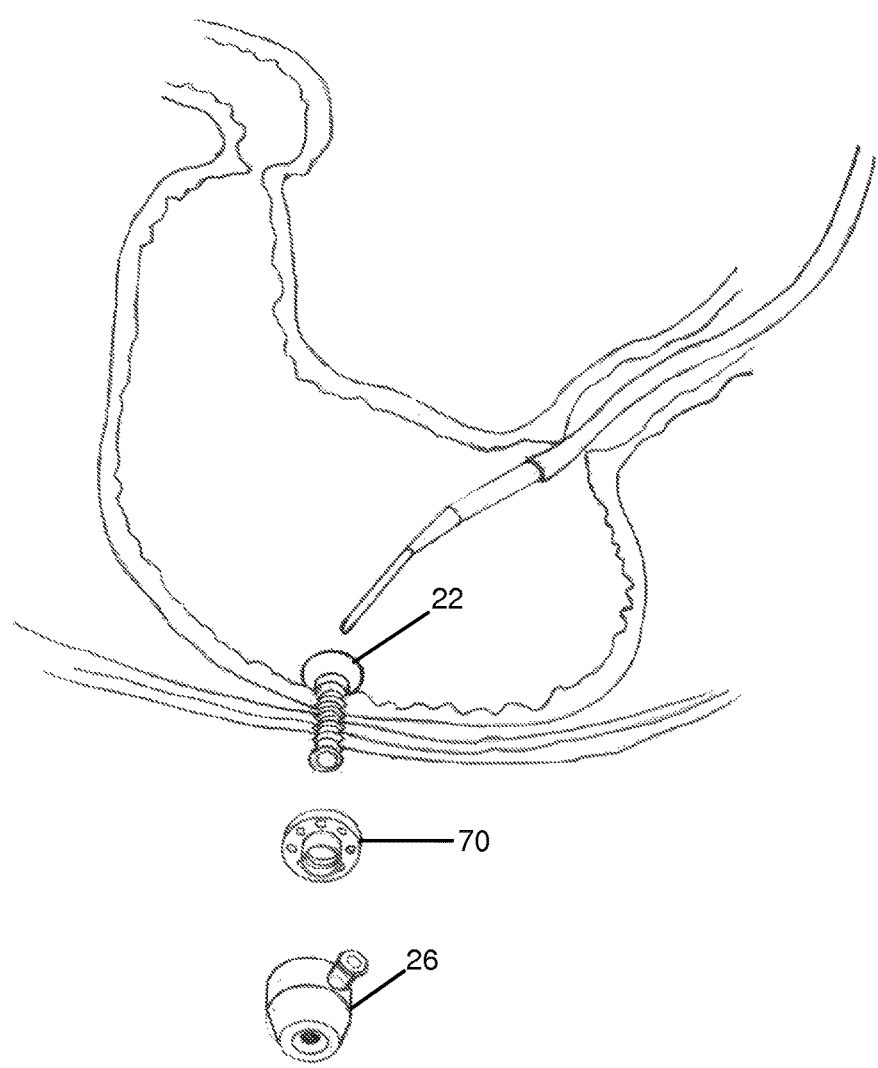
FIG. 4 is a perspective view of the surgical device in place within a patient and removal of the introducer device in a cross section view of the patient.
Figure 5:
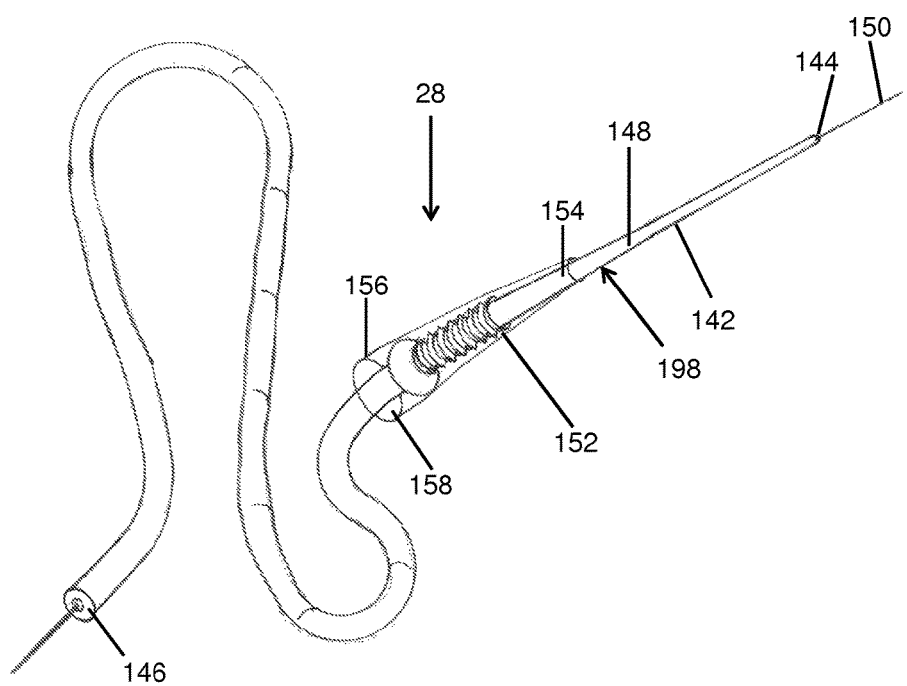
FIG. 5 is a perspective view of the introducer device preloaded with the surgical device.
Figure 6:
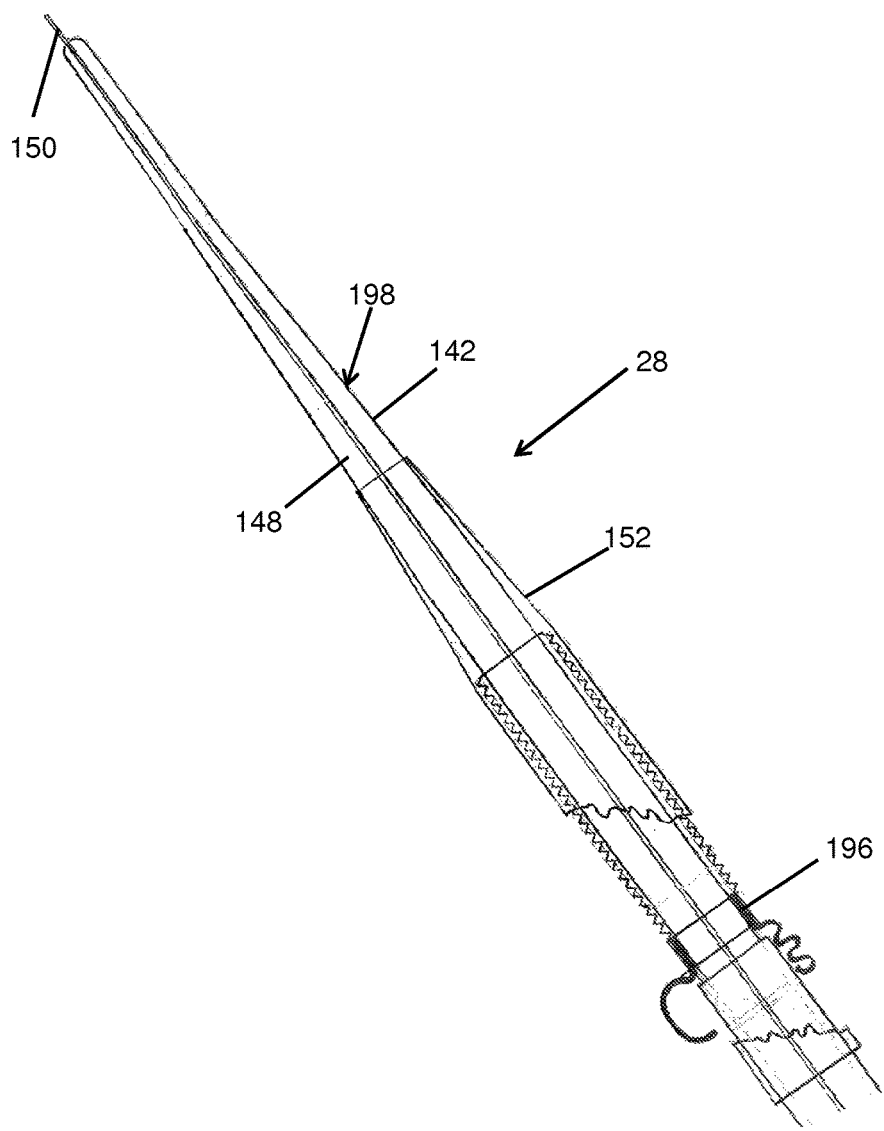
FIG. 6 is a side view of the proximal end of the introducer device preloaded with the surgical device.

A transabdominal gastric cannula surgical system 1 and method is illustrated in FIGS. 1-4, 13, 14, 17, 19 and 20 installed trans-abdominally in a patient to extend between the stomach 10, located within the abdominal or peritoneal cavity 12, abdominal wall 14 and skin 16, and exiting through a surgically created opening or stoma 18. The cannula surgical system 1 (cannula system) includes a cannula 20, an internal anchor assembly 22, an external anchor assembly 24, a closure cap assembly 26, and an insertion tool 28 (FIG. 4).

Figure 1:
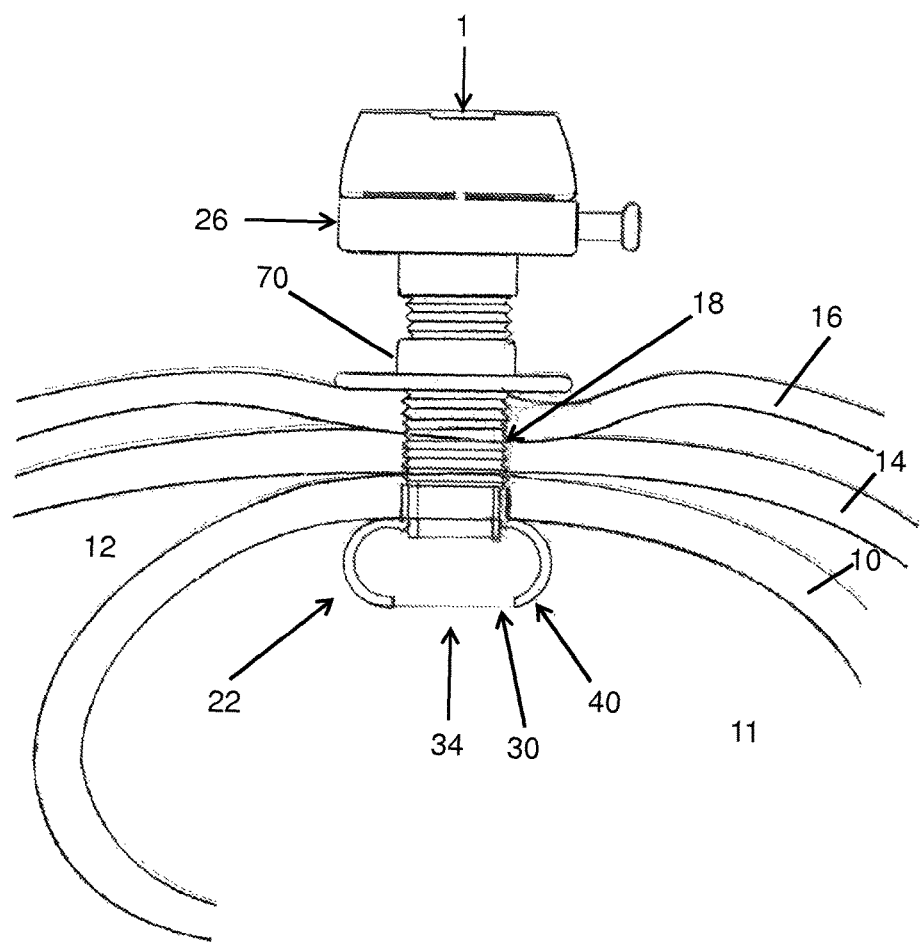
FIG. 1 is a schematic representation of a transabdominal gastric surgical device in accordance with the invention shown installed within the stomach of a patient.
Figure 2:
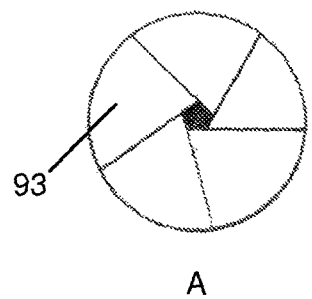
FIGS. 2 A, B, C, D, and E is a side elevation view of the seal (A), the cap (B), the closure disc (C), the external anchor (D), and the cannula with an internal anchor (E).
Figure 2:
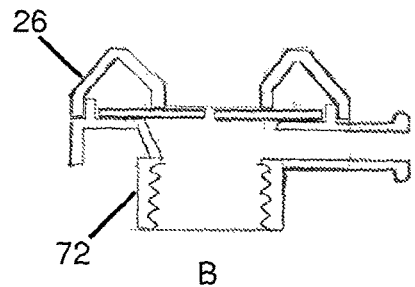
Figure 2:
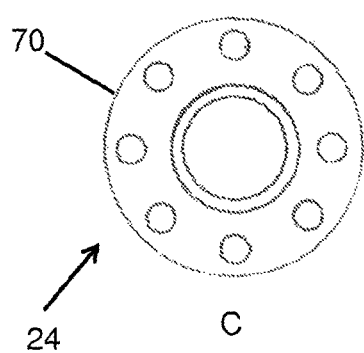
Figure 2:
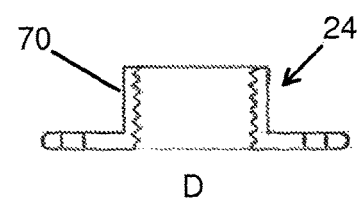
Figure 2:
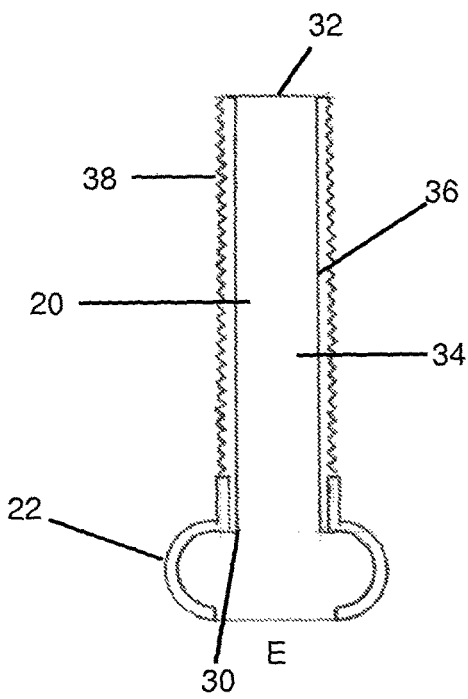

The cannula 20 has a normally inner end 30 and a normally outer end 32 and a sidewall 36 extending between the ends. The sidewall 36 circumscribes a cannula lumen or working channel 34. An internal anchor assembly 22 is connected at or adjacent to the cannula inner end 30. The external surface of the outer end 32 extends above the outer abdominal wall provided with fastening means such as helical threading 38. As illustrated in FIGS. 1 and 4, the cannula is positioned in a patient with the internal anchor 22 deployed adjacent the interior surface of the wall of the stomach 10 of a patient.

The cannula 20 is configured to allow access within the gastric lumen 11, peritoneal, or retroperitoneal space for medical procedures. The cannula is configured with a length between 4 cm and 30 cm. In an additional embodiment the cannula will be between 6 cm to 10 cm. In an additional embodiment the cannula can be 5, 6, 7, 8, 9, 10, 11, 12, 13, 14, 15, 16, 17, 18, 19, 20, 21, 22, 23, 24, 25, 26, 27, 28, 29 or 30 cm. The cannula is also configured with diameter of between 3 mm and 70 mm. In an additional embodiment the cannula will have a diameter of between 5 mm and 20 mm. In an additional embodiment the diameter can be 10, 15, 20, 25, 30, 35, 40, 45, 50, 55, 60, 65, or 70 mm. The cannula is made of any material known in the industry that is safe for patient use in a medical procedure. The cannula is composed of material that has the desired rigidity and flexibility and including but not limited to the materials such as medical grade silicone, polyvinyl chloride (PVC), plastic, rubber and any similar material known in the industry. The flexible nature of the material is important for the initial placement of the cannula within the patient. The rigidity is important while using the cannula during a procedure. In an additional embodiment the cannula may be composed of a more rigid material but still with the flexibility required for the initial placement with the patient.

Figure 11:
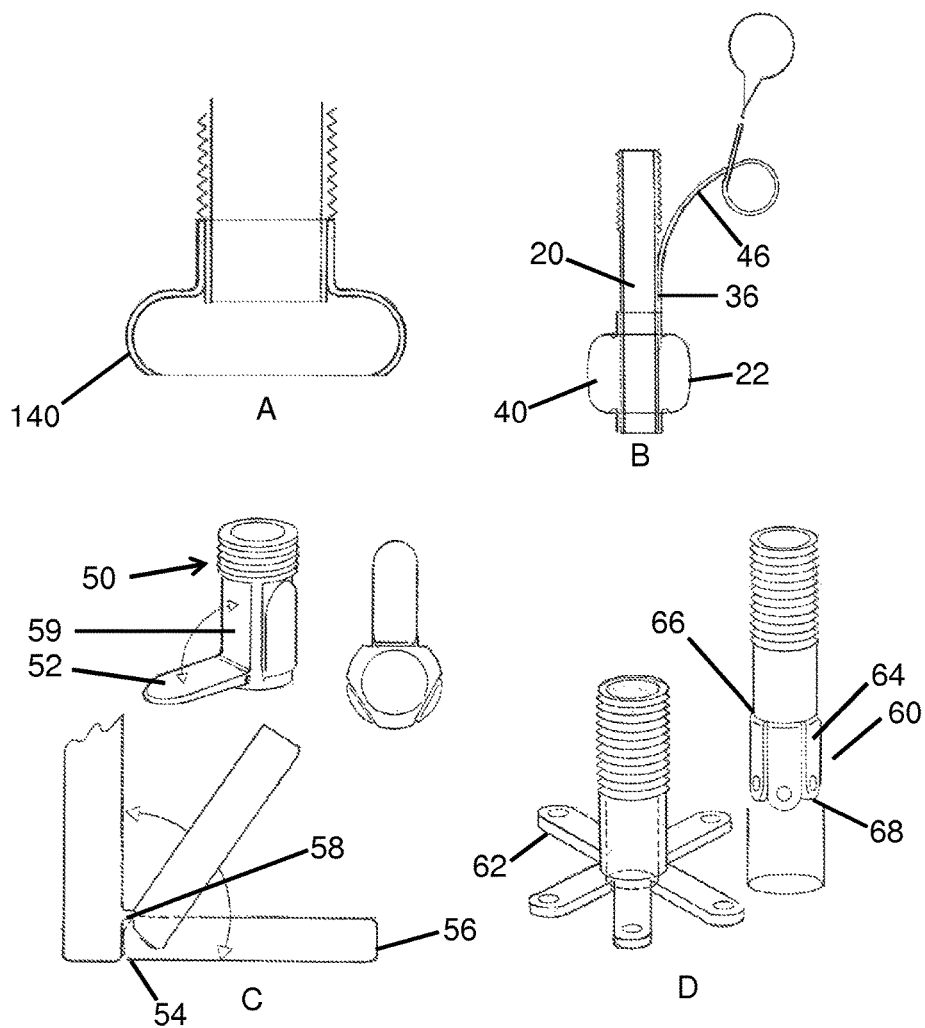
FIGS. 11 A, B, C, and D are side and perspective views of the cannula and internal anchor of the surgical device.

The system 1 internal anchor 22 may be of any suitable configuration known in the art, such as an expandable balloon, bumper, or umbrella (or any similar anchor system known in the industry) as illustrated in FIG. 11. The internal anchor is configured to allow for deployment against the interior surface of the gastric wall to retain the lower end of the device in position at the stomach wall and reduce movement during a procedure. The internal anchor 22 is also configured to be removable, for example, by retraction. A balloon-type anchor is illustrated in FIG. 11 to include a balloon element 40 for receiving the cannula 20 there through in circumscribing or encircling relation. An inflation tube 46 extends outwardly from the balloon element 40 for use in inflating the anchor 22 to a deployed configuration. The inflation tube 46 is held in place against the outer surface of the cannula sidewall 36. The system can further include a sealing mechanism, such as a plug, valve, stopcock, or any similar sealing mechanism known in the industry. The sealing mechanism, such as the plug can be provided to maintain inflation of the balloon after deployment. The balloon element 40 is illustrated in the drawing figures positioned in superior relation to the cannula inner end 30 or in addition may be flush with the cannula inner end 30. In another aspect, the balloon element may be constructed in a ring formation, without a lower neck, to enable positioning adjacent the intragastric portion of the cannula inner end.

A bumper type internal anchor assembly 140 is illustrated in FIG. 11A. The body of the bumper internal anchor 140 is configured to extend out from the cannula 20. The bumper internal anchor allows for the secure placement of the cannula against the internal gastric wall. The bumper internal anchor is configured with a size ratio of 4:1, (bumper internal anchor:cannula), with the bumper internal anchor being larger than the cannula to ensure a secure placement with the gastric wall. In another embodiment the bumper internal anchor can be 1:1, 2:1, 3:1, 5:1, or 6:1 (bumper internal anchor:cannula) dependent on the desired use. In an additional embodiment the bumper internal anchor can have a diameter of between 12 mm to 130 mm. In an additional embodiment the bumper internal anchor diameter of 15, 20, 25, 30, 35, 40, 45, 50, 55, 60, 65, 70, 75, 80, 85, 90, 95, 100, 105, 110, 115, 120, or 125 mm. The bumper internal anchor may be composed of any material known in the industry that is safe for use with patients, including but not limited to silicone, PVC, plastic, rubber, or any other material known in the industry.

An umbrella-type internal anchor assembly 50 is illustrated in FIG. 11C to include a plurality of wings or legs 52, each having a base 54 and an opposed tip 56. A hinge member 58 connects each leg and is connected at its base 54 to the cannula sidewall 36. The external surface of the cannula sidewall 36 includes a plurality of longitudinally oriented spacers 59 for receiving the legs 52 there between when they are in an upwardly folded, non-deployed position.

An alternate umbrella-type anchor assembly 60 is illustrated in FIG. 11D to include a plurality of legs 62 connected at their bases 64 to hinge member 66 configured to fold downwardly when non-deployed, so that the legs 62 extend with tips 68 downward, beyond the cannula inner end 30. The respective legs 52 and 62 of the umbrella-type anchor assemblies 50 and 60 are illustrated as being of unitary construction with the cannula 20, and interconnected by respective living hinges 58 and 66. In another aspect, the anchor may be separately constructed and connected to the cannula 20. The legs are configured with sufficient length to aide in anchoring the system. The hinge(s) and anchor may be composed of any material known in the industry that is safe for use with patients, including but not limited to silicone, PVC, or any other material known in the industry.

Figure 12A:
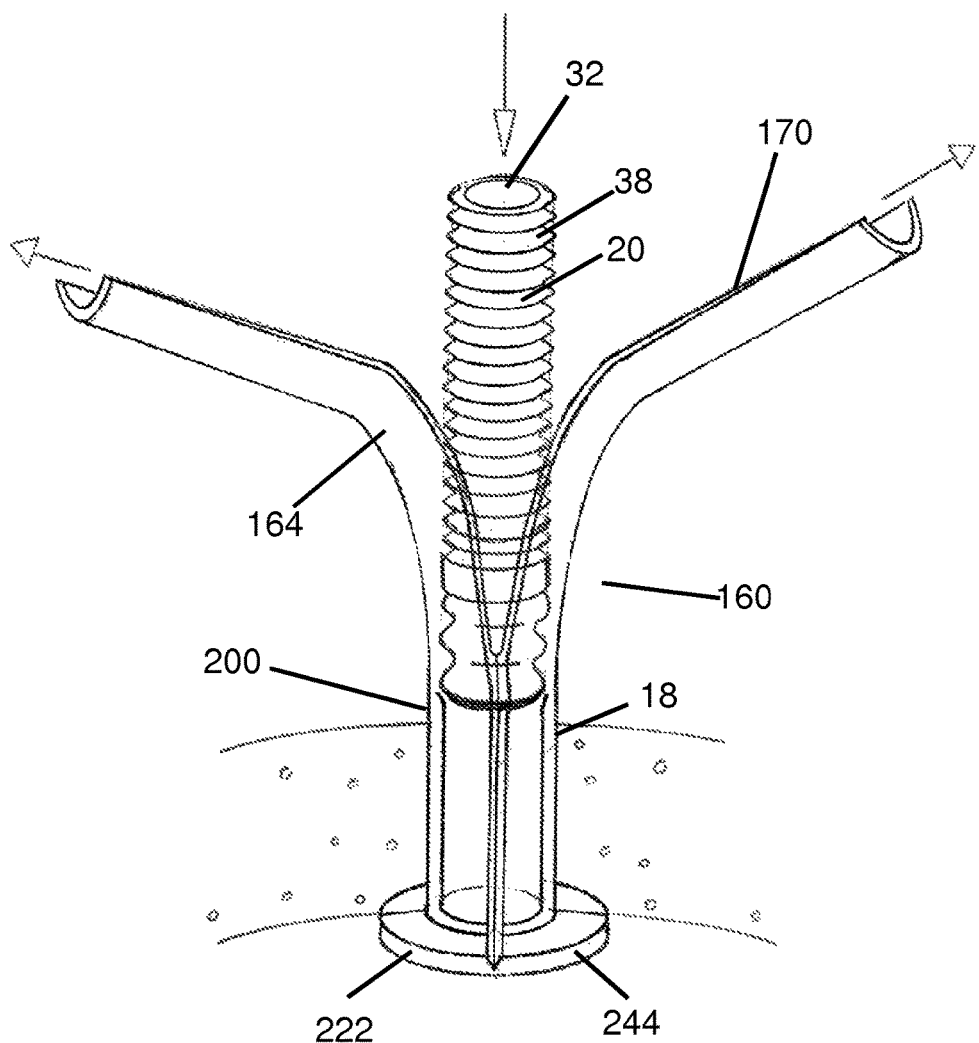
FIGS. 12 A and B are perspective views of the surgical device in conjunction with a tear away PEG.
Figure 12B:
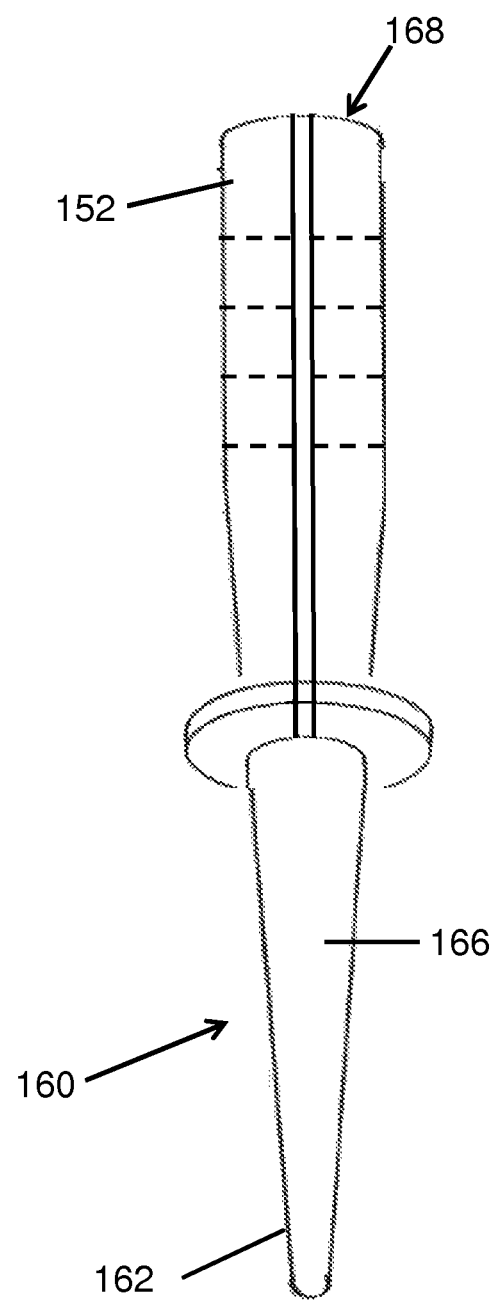
Figure 13:
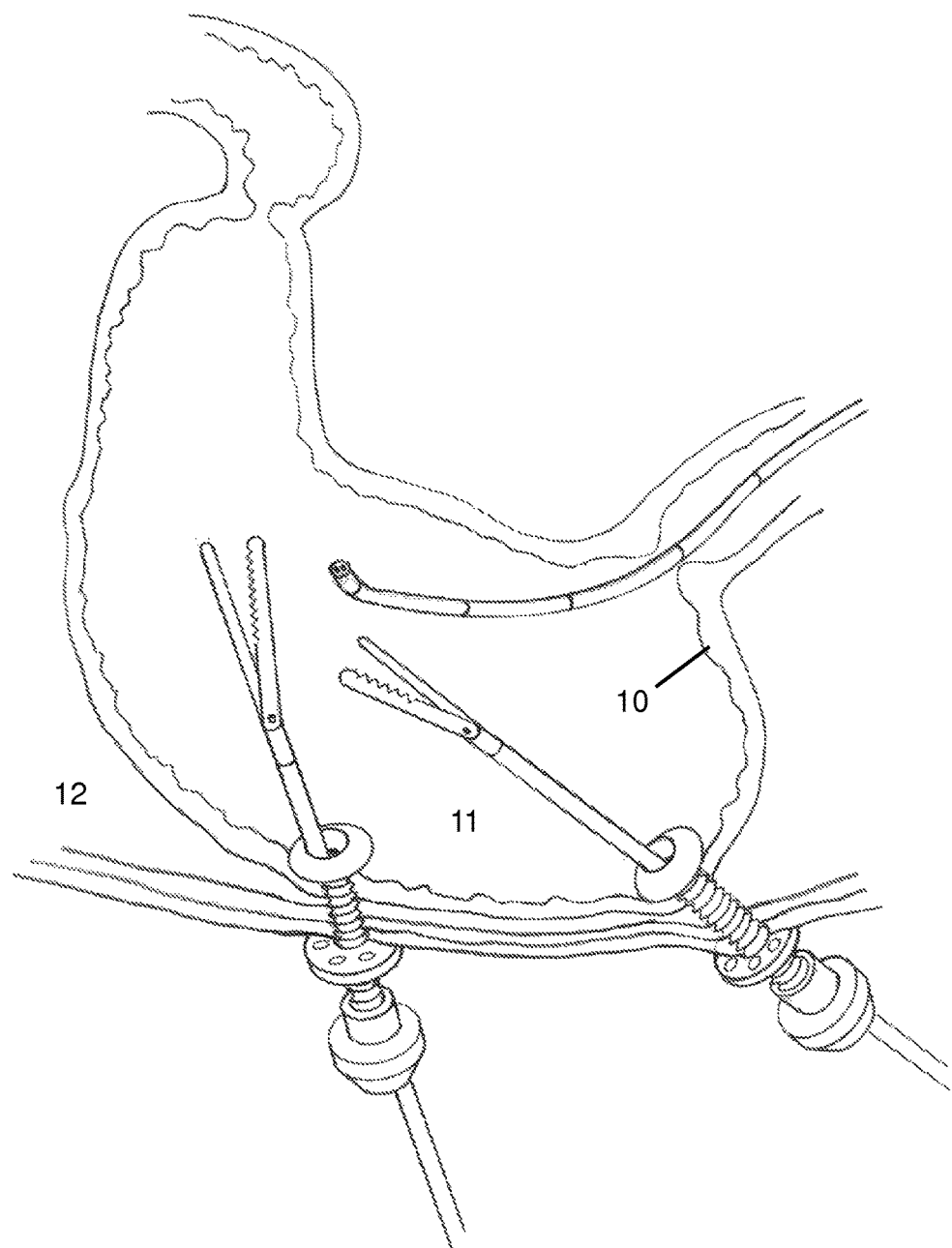
FIG. 13 is a schematic view demonstrating use of the surgical device(s) and triangulation within the gastric lumen.
Figure 14:
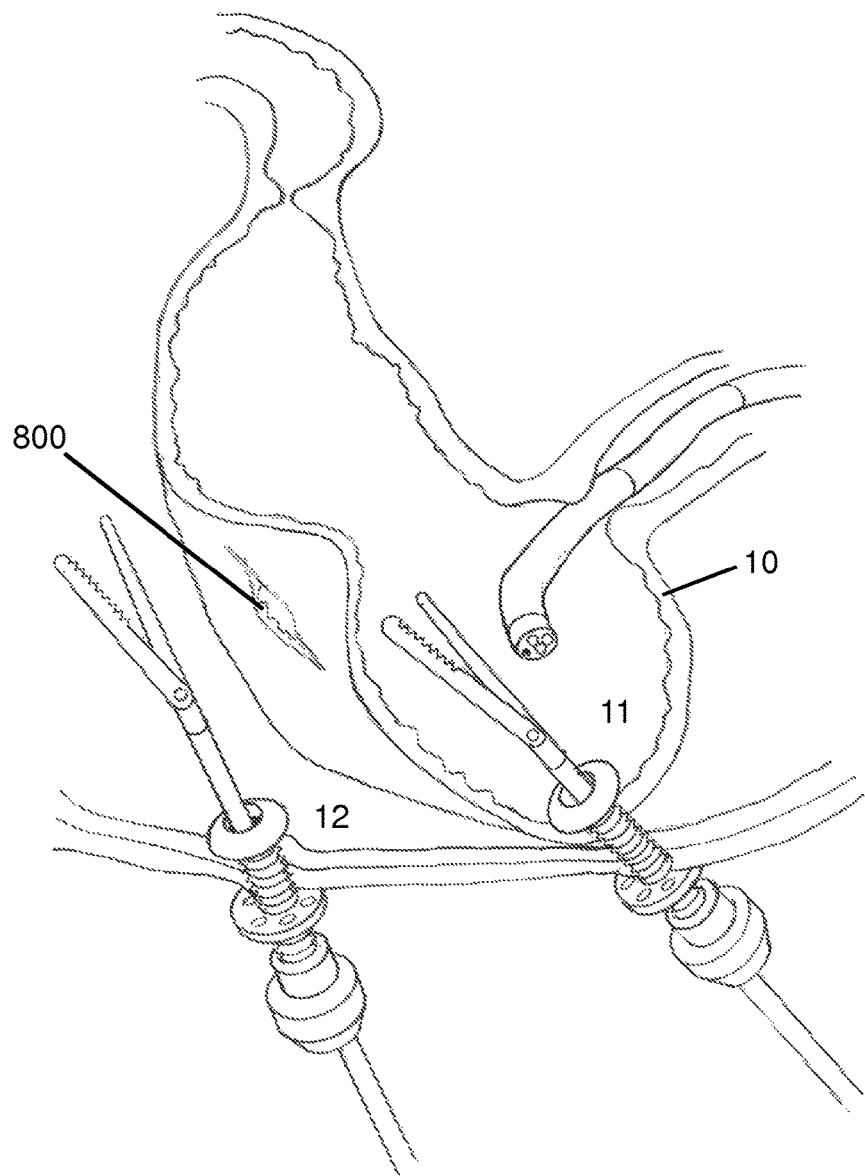
FIG. 14 is a schematic view demonstrating use of the surgical device(s) within both the gastric lumen and the extralumenal cavity.

In an additional embodiment as illustrated in FIG. 12 the cannula 20 is installed inside a PEG tube 200 with the PEG internal anchor 222 deployed inward of the gastric wall.

Figure 7:
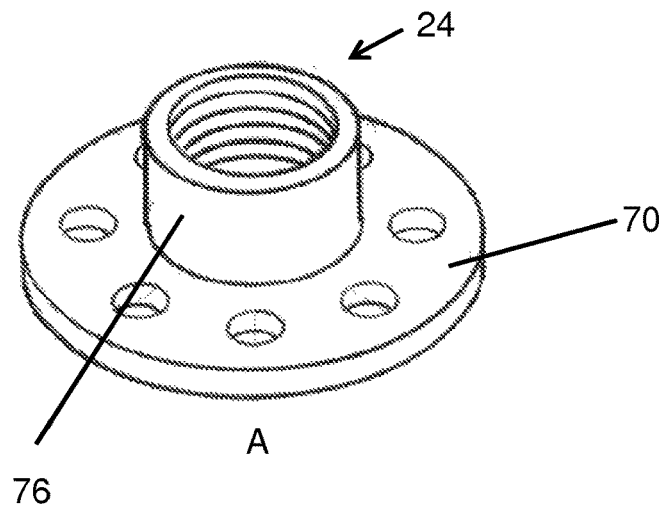
FIGS. 7 A, B, and C are perspective, top, and side views of the external anchor.
Figure 7:
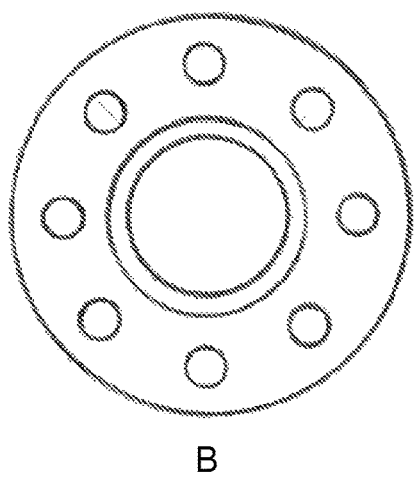
Figure 7:
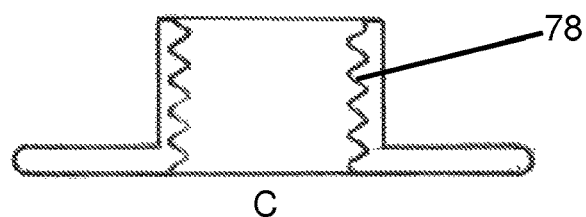

As best shown in FIG. 7, the external anchor 24 assembly includes an anchor disc 70. The anchor disc 70 includes a neck 76 configured for removable connection over the cannula 20. The anchor disc 70 is installed over the cannula 20 in a position in contacting relation with the skin surface 16 of the patient. The neck 76 is configured to extend above the planar surface of the disc. The length of the neck 76 is between 1 cm and 4 cm, (including a length of 1 cm, 2 cm, 3 cm, or 4 cm). In additional embodiments the neck can be greater than 4 cm or less than 1 cm. The diameter of the neck 76 is configured to allow it to fit over the cannula and create connection with the cannula. The anchor disc is composed of any material known in the industry including, but not limited to silicone, PVC, plastic, aluminum, surgical steel or combinations thereof. After placement of the external anchor the cannula 20 is then safely and securely set in place to allow for passage and use of surgical instruments through the working channel or cannula lumen. The anchor disc 70 allows for securing the abdominal wall and/or abdominal wall and gastric wall into position. The anchor disc 70 cooperates with the internal anchor 22 assembly to fasten the abdominal wall to the gastric wall. The use of the internal and external anchor in conjunction with each other allows for a safe, stable, and reliable working channel while the system is held in position and stabilized against both the gastric and abdominal wall. The adjustability of the external anchor allows for safely stabilizing despite the individuals patients anatomic variations and sizes. In additional embodiments the anchor disc can be any shape known in the industry including but not limited to square, hexagonal, octagonal, pentagonal, oval, triangular, cross, or any shape that allows for the external anchoring of the device.

In additional embodiments the external anchor can include a plurality of discs. The plurality of discs is positioned to create a connection with each other at the skin of the patient to anchor the cannula surgical device. The discs can be interchangeable with various numbers of sizes of ports, attachments structure for attachment of external interchangeable discs with access ports to a central cannula, and attachment structure for attachment of the discs to each other. The discs include cannula-attachment structure in the form of threading for mating engagement with threads 38 on the external surface of the cannula sidewall 36. In another aspect, the central apertures of the discs may be sized to be held in place on the outer surface of the cannula sidewall 36 by a friction fit, or they may include other attachment means such as ridges, bumps, nuts and bolt mechanism, slots or any other suitable structure. The discs may also include disc-to-disc and disc-to-cannula attachment means such as threading 78 or bayonet fittings or any other suitable structure to enable releasable connection of each disc to the adjacent disc or discs to facilitate close stacking while permitting decoupling and substitution of discs.

Figure 10:
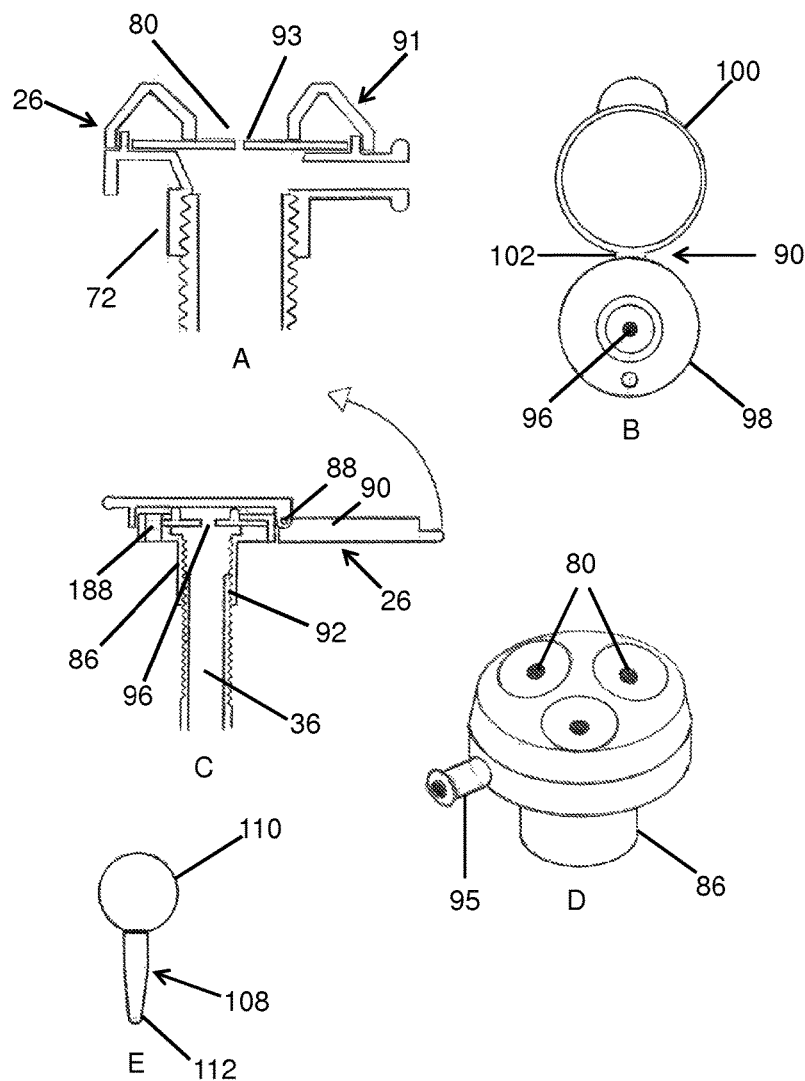
FIGS. 10 A, B, C, D, and E are side and perspective views of the surgical device cap or top (A, B, C, D) and the plug.

The system 1 in an additional embodiment can include an array of caps having various diameters, depths and arrangements of the instrument access ports 80 within the cap as illustrated in FIG. 10. Some caps may include only a central aperture for receiving the cannula 20. Other caps may include a single access port 80. Two or more ports 80 may be positioned in parallel relation for vertical access as shown in FIG. 10. A plurality of ports 80 may be positioned, with some vertically oriented ports and some angular ports that subtend an acute angle to the adjacent skin surface.

The instrument access ports 80 within the cap are formed of a flexible synthetic resin or other material or combination of materials that may include a slit or other formation enabling them to maintain a closed sealing relation when not in use to prevent entry of contaminants into the cannula lumen 34 or air leakage from the stomach via the cannula lumen 34.

Figure 8:
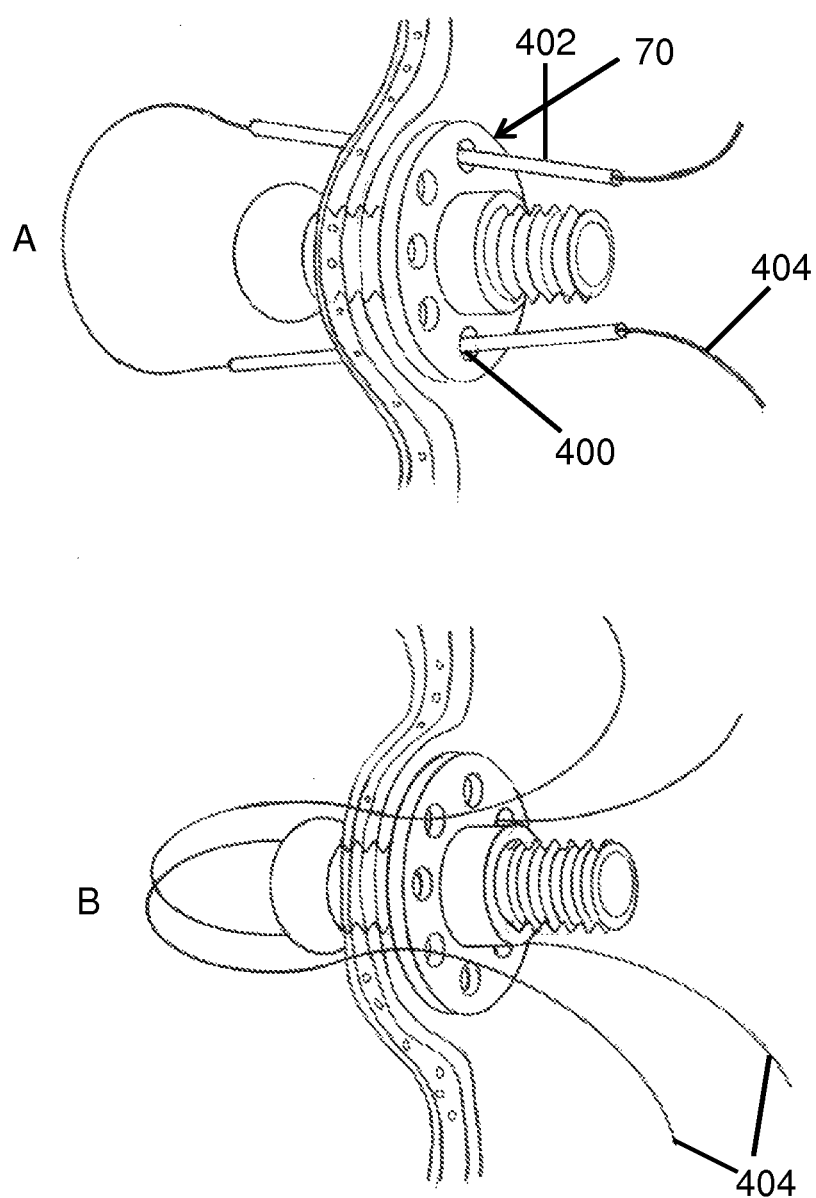
FIGS. 8 A and B are perspective views of the external anchor with a closure configuration to demonstrate the closure of the created opening.
Figure 9:
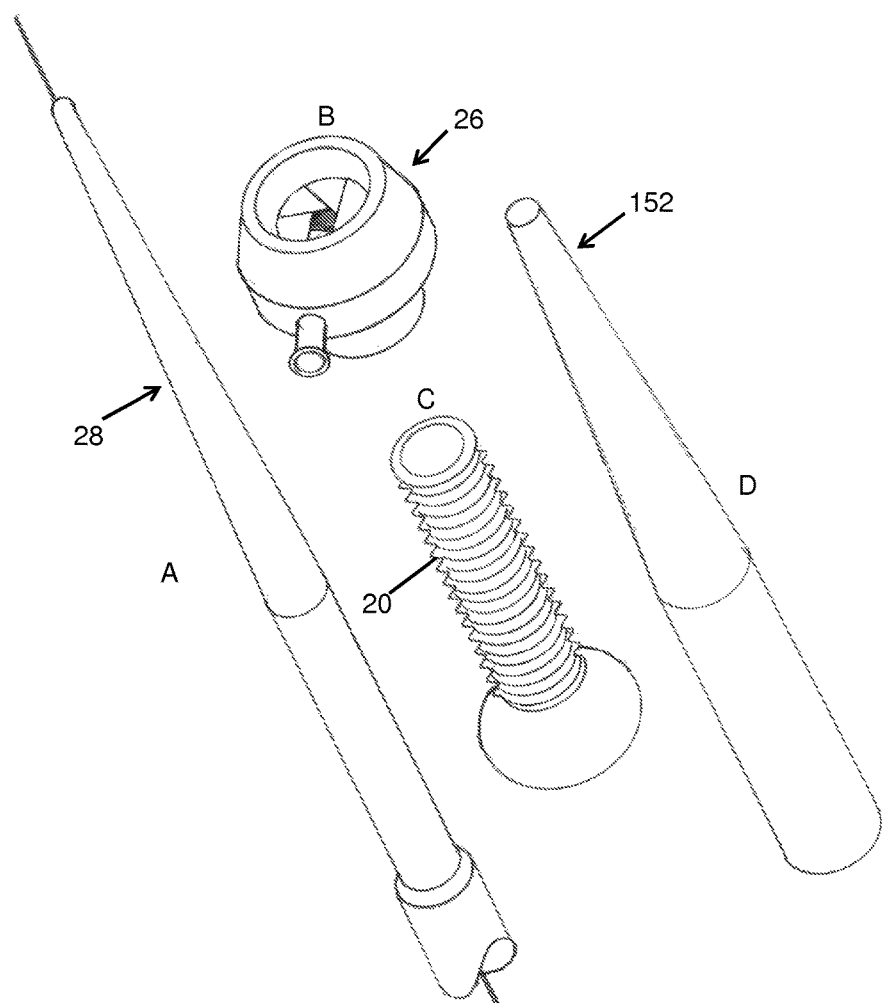
FIGS. 9 A, B, C, and D are perspective views of the introducer device and the surgical device.

In one embodiment the anchor disc 70 will include a pre-positioned closure configuration as illustrated in FIG. 8. The anchor disc 70 includes opening on the external disc for use with a needle catheter guide. The pre-positioned closure device allows for a suture to be placed through the catheter and into the gastric lumen through the abdominal wall and gastric wall. A suture grasper is placed through a second catheter to aide in grasping the suture placed in another catheter. Repeating this process results in the pre-position of the closure sutures for use when the cannula 20 is removed.

As best shown in FIG. 10, the cannula closure includes a cap 91 at the external end of the cannula. The cap 91 is configured to attach to the cannula to aid in creating a working channel to allow access for the surgical instruments to enter the gastric space. The cap is configured to include an inner memory seal 93 with at least a single layer of a silicone layer with an opening. In another embodiment the inner memory seal can include two or more layers. The inner memory seal 93 allows for airtight passage, removal, and exchange of multiple instruments that can pass through the cap into the working channel and finally into the gastric lumen or extralumenal spaces. The cap is configured with at least a single lumen. In another embodiment the cap can include a plurality of lumens or opening as demonstrated in FIG. 10D to allow for a plurality of instruments during a procedure enabling triangulation by the user. The cap can also be configured with a port 95 to allow for gas insufflation, such as $CO_2$ or air, into the intra-gastric and intraperitoneal pressure. The port 95 can be used for gas insufflation and/or monitoring the pressure of the patient during the procedure.

In another embodiment the cap will be a cannula closure sealant assembly 26 and will include a tubular stem 86, having a hinged flange 88 at one end. The flange is hinged connected to a removable cap lid 90. The stem 86 includes internal threading 92 for mating engagement with the upper threaded portion of the cannula 20. The upper surface of the flange 88 includes an annular or ring seal or gasket 93 having a central aperture 96, both axially aligned with the stem 86 of the closure. As illustrated, the cap lid 90 has a generally circular configuration with outer and inner surfaces. In an additional embodiment the cap lid 90 can have a hexagonal configuration or any shape used in the art. An upstanding lip 98 is disposed at the perimeter of the inner surface. A tab structure 100 extends outwardly beyond the lip 98 to facilitate grasping of the cap lid 90 by a user. The cap lid 90 is pivotally connected with the flange 88 by a hinge member 102, which may be of conventional construction as shown in FIG. 10, or it may be constructed as an integral or "living" hinge, or in any other suitable manner. The cap lid 90 may also be connected to the flange 88 by a vertical pivot member (not shown) positioned at the perimeter of the flange, enabling the cap to be pivoted laterally in the same plane to expose the lid flange 88. The flange and the cap lid 90 may each include respective small magnets 188 which are aligned for mutual attraction when the cap lid is in the closed position covering the flange 88. A plug 108 is provided for insertion into the aperture 96 to seal off the stem 86 and communicating working channel 34 of the cannula. The plug 108 includes a graspable upper portion 110 surmounting a tapered stem 112. These may have the taper and sphere configuration illustrated in FIG. 10E, or any other shape providing ease of insertion and removal.

An alternate form of cannula closure will include a flange provided with a generally conical central indention for mounting an instrument seal member such as a gel seal. The cap lid is formed of a flexible material and is configured to overlie the perimeter of the flange, and provide a raised bumper defining a central aperture that is axially aligned with the instrument seal. The inner surface of the cap includes an axially projecting sealing member that is sized and shaped for reception in the aperture when the cap lid is in a closed position. While a generally obconic central sealing member is disclosed, the seal may be of any shape that is suitable to accomplish sealing a correspondingly shaped aperture.

Another alternate construction of the cannula in which the cannula is constructed to include a series of folds, windings or compressions of the cannula material, such as a memory wire. The cannula is constructed to contract or expand radially. Allowing the diameter of the cannula to expand or contact. The cannula is composed of radially compressible construction and material to allow for expansion of the working channel diameter to accommodate a desired medical instrument. Such a radially expandable construction is particularly advantageous in enabling the cannula to pass more easily into a small surgical opening or stoma 18, or into a PEG tube which may later be enlarged.

An insertion introducer tool 28 is illustrated in FIGS. 4-6 and 9 to include an elongated core element 142 having an insertion end 144 and a graspable end 146, with a central lumen 148 extending between them. The insertion tool is configured to include a dilator-type placement tool with a tapered proximal end and increase in size and diameter to the distal end. The general configuration is of a conical shape with the central lumen and cylindrical core. The lumen is sized to receive a guide wire 150, which is threaded into the lumen and extends outwardly at both ends 144 and 146 of the core. The tool further includes a guide wire 150 used to guide the insertion tool 28 into position and manipulate it during use. It may remain in place following removal of the tool for use in controlling the cannula 20. A generally conical dilator shield 152 extends forwardly from the graspable end of the core 142 in surrounding relation. The shield 152 has the form of a tapered tube, with a narrow or tapered insertion end 154, an opposed wider end 156 and a lumen 158 there between. The shield is configured to allow a portion of the core 142 to protrude forwardly out from the tapered end 154, which may be taped, friction fit, or stitched or twisted and screwed to the core to hold it in place. The shield is constructed of a flexible material, such as a synthetic resin to facilitate dilation of the opening through which it is inserted without causing damage to the tissue.

The tool further includes a fixed or removable front bumper 198 sized and designed recessed area at its proximal end to allow for the pre-loaded placement of the cannula to allow for the seating and flush configuration of the cannula on the introducer tool.

In an additional embodiment the introducer tool will include a removable/adjustable front bumper loaded onto the introducer at the proximal end of the working channel of the cannula. The inclusion of the bumper increases stability and reduces friction of the cannula upon introduction within the patient. The removable front bumper also allows for ease of release of the cannula from the introducer.

An alternate construction of an insertion tool 160 is illustrated in FIG. 12, in which a core 162 and threads of the cannula are not covered by a flexible shield 164. The core includes a tapered end 166 and a wide end 168 as previously described. A plurality of longitudinally oriented scores or grooves 170 extend along the length of the PEG. Once the cannula 20 has been positioned, the grooves 170 enable the PEG walls to be easily split stripped away toward the wide end 244 to expose the cannula 20 along with the internal anchor 22. The cannula is configured for placement with the use of a modified strippable PEG 2. After tearing away the removable portion of the PEG tube, the cannula may be introduced. In another aspect, where a radially compressed cannula is employed, the cannula is expanded to a desired diameter after tearing away the removable portion of the PEG tube. The system includes an introducer dilator-type placement tool that is tapered at its proximal end and increases in size and diameter to its distal end having a generally conical shape with a central lumen equipped with a generally cylindrical core element. A guide wire extends through a central lumen of the tool. The introducer placement tool has a unique & specially sized and designed recessed area at its more proximal end. Once the insertion tool 28 is in place though the PEG tube 2, the user withdraws the insertion tool core 142 from the cannula 20 backwardly externally from skin surface level and the internal bumper of the cannula 22 is positioned against the gastric wall 10 and adjusted by direct endoscopic vision while the tear away internal bumper of PEG 222 is removed once tear is complete. After the initial insertion the inserter core 142 is removed externally and the guide wire 150 remains in place to provide a means of control over the cannula 20.

The system 1 may be supplied in the form of a kit, including one or more cannulas 20, including internal and external anchor assemblies 22 and 24, insertion tools 28, discs 70, 72, 24 (which may be supplied in any other suitable quantity), and cap assemblies include 26 and 90.

In a method of use as illustrated in FIGS. 3 and 4 a user loads a cannula 20 onto an insertion tool 28 by aligning an inserter core 142, equipped with a central guide wire 150, with the cannula lumen 34. The guide wire length should be adequate to allow manipulation of the external and internal portions of the introducer and the cannula system with full control both from the oral and abdominal sides. Typically the length will be at least 300 cm. In an additional embodiment the length can be less than 300 cm. The configuration of the guide wire will be a 1.5 mm diameter (such as a Savary Gilliard guidewire) along with a floppy tip on the introduction side from the exterior abdominal wall that can be later grasped with a polypectomy snare extending from the endoscope and removed via the oro-pharynx. The cannula is preloaded onto a recessed area of the desired length and width to allow the system to seat itself flush with the insertion tool 28. The user slides the cannula 20 over the core 142 until the cannula inner end 30 reaches the backstop 196 of the core 142. In order to receive the tapered shield 152, the internal anchor assembly 22 may or may not be in a non-deployed configuration depending on its specific type. The user ensures that the balloon-type internal anchor 22 has the balloon element 40 deflated and flattened against the lower portion of the cannula 20 adjacent the inner end 30 as shown in FIG. 8. The user next aligns the flexible shield 152 with the core and passes the core through the wide end 156 and out through the tapered end 154 until the shield reaches the top of the internal bumper without a gap. It is also possible that a second cannula system can be inserted either in sequential order or in parallel with the first cannula system.

If the cannula 20 is equipped with an umbrella-type anchor, the user must ensure that the legs 52 are shifted into an upwardly folded position against the lower portion of the cannula 20 adjacent the inner end 30. If the cannula 20 is equipped with an internal anchor having downwardly folding deployable legs 62, the user must ensure that the legs are folded in a downward direction to extend beyond the cannula inner end 32. The user next slides the guide wire and inserter core 142 into the wide end 152 of the flexible shield 152 and out the tapered end 154, continuing until the wide end of the shield is stopped by the graspable end of the core.

The guide wire 150 with the entrained tool 28 containing the cannula 20 may then be advanced into the throat of a patient, passed through the oral-pharynx, down the esophagus and into the stomach. Advancement of the guide wire and tool is continued through the surgical opening 18 previously created between the stomach 10, the abdominal wall 14 and the exterior surface of the skin 16. Alternatively, the guide wire may be employed to pierce the wall of the stomach and create a small opening which is then gradually dilated or enlarged by the core. In such applications, the core may be equipped with a tapered tip. As the core is advanced it enlarges the opening to receive the tapered end of the tool 28. The opening is further enlarged by continued passage of the tool through the opening until it reaches the wide end of the tool, eventually emerging through the outer surface of the patient's skin. In this manner, a user may employ the tool 28 to create a surgical opening without the need for use of a separate surgical tool or instrument.

Once the insertion tool 28 is in place though the stoma 18, the user withdraws the flexible shield 152 externally and the insertion tool core 142 from the cannula 20 backwardly, into the stomach 10. While the inserter core 142 and shield 152 are removed, the guide wire 150 remains in place to provide a means of control over the cannula 20 during the procedure. Where the tool is used with a tear-away PEG tube 164, the core 162 is externally removed after tearing the PEG tube along the score lines 170 and removing the strips separately through the stomach 10, or outwardly through the stoma 18.

A user deploys the balloon-type anchor by connecting a source of pressurized air to the inflation tube 46 and inflating the balloon element 40 to a desired size. The umbrella-type anchors 50 and 60 deploy automatically when the flexible shield is removed, which allows the legs 52 or 62 to return to their normal outstanding positions. The deployed internal anchor assembly 22 is then positioned in contact with the inner surface of the gastric wall. Once the outer end 32 of the cannula has passed through the external opening or stoma, the insertion tool may be backed out of the opening along the guide wire 150 and through the stomach. The guide wire 150 remains in place following placement of the cannula 20 and removal of the tool 28 for use in adjusting and controlling the positioning of the cannula 20.

A user selects one or more discs from an array of discs 70, 72, 24. The disc central apertures 76 include helical threading 78 for mating engagement with the threads 38 on the external sidewall of the cannula 20. The user aligns the central aperture 76 of a selected anchor disc 70 with the cannula sidewall 36 and threads the disc onto the cannula. The user continues to tighten the anchor disc 70 onto the cannula 20 until the internal anchor assembly 22 urges the gastric wall into contact with the abdominal wall 14. A single disc 70 serves as an external anchor 24 assembly which cooperates with the internal anchor 22 to fasten the gastric wall to the abdominal wall. Where the discs are constructed to include structure enabling them to be fastened together, they may also be installed by selecting the discs to be used, arranging them in order, fastening them together and threading them onto the cannula 20 simultaneously, as a unit. In another aspect, one or more discs may be employed as an external anchor and additional discs may be installed in spaced superior relation on the cannula 20.

As illustrated in FIG. 10, the cap disc as is equipped with multiple sealed instrument ports and that may subtend a variety of angles with the cannula lumen 34. In this manner, surgical instruments and medical devices may be introduced into the working channel 34 at a plurality of angular orientations. In addition, the instrument port seals may be constructed of an elastomeric material to permit an expanded range of movement and/or rotation of the instruments within the channel. In one aspect, a cannula closure assembly 26 may be installed instead of the discs 70, 72 and 74 and may include a central access port. In one aspect, a cannula closure assembly 26 may be employed as an adaptor and installed above an external anchor disc 70, with additional discs installed above the closure assembly 26. In another aspect, a cannula closure element 26 may be installed outboard of one or more discs 70, 72, and 74, either alone or in combination.

Once installed in the body of a patient, a physician employs the device 1 by inserting medical instruments and devices, such as instruments for surgery, biopsy, suturing and stapling, cannula, and laparoscopic devices through the ports 80 at various angular orientations and into the stomach 10 of a patient to perform a medical procedure. Multiple instruments and devices may be used for triangulation, obviating the need for additional surgically created openings in the patient's body. An endoscope may also be inserted via the patient's esophagus and endoscopic instruments may be inserted, used and triangulated concurrently with laparoscopic instruments inserted via the cannula 20. In one aspect, a plurality of device 1 may be installed through a plurality of openings as previously described, thereby providing multiple instrument access ports. An instrument may be withdrawn from an access port 80 at any time and a new instrument or device inserted through the same or a different port. The physician may use the instruments to construct an opening from the stomach into the abdominal cavity, thereby acquiring access to other intraperitoneal organs such as the pancreas, liver, gall bladder, small and large bowel, or to gain access to the retroperitoneal area and organs such as the pancreas therein, or virtually any other location in the body of a patient. From the peritoneal cavity, the physician may bring a portion of another organ into the stomach for a surgical procedure. The physician may also create an opening into a selected organ for a surgical procedure. The stomach provides a sterile region in which to perform surgical procedures due to its highly acidic environment.

Advantageously, the system 1 provides ready intragastric access for a wide variety of procedures in the organs or in the areas of, for example, the esophagus, stomach, duodenum and proximal small bowel. Multiple laparoscopic instruments may then be inserted alone or simultaneously through the cap containing the memory sealant then through the lumen of the cannula into the gastric lumen 11. The system also permits access for a wide variety of intraperitoneal surgical procedures in the organs or in the areas of, for example, the gallbladder, spleen, pancreas, transverse colon, remaining colon, including the appendix and rectum, liver, small bowel, as well as retroperitoneal access to organs and areas such as the pancreas, kidneys and adrenal glands. An endoscope may also be deployed at the same time through the esophagus and into the stomach 10. If the inner bumper is adjusted to the inner aspect of the abdominal wall then instruments will pass into the cap then through the lumen of the cannula into the peritoneal cavity 12.

The use of the introducer and cannula system is a minimally invasive for procedures in the peritoneal cavity via the gastric lumen allowing for anterior gastrostomy access. The anterior gastrostomy 800 is formed after standard placement of the cannula device by pulling the internal anchor through the gastric wall to rest against the inner gastric wall. The procedure can include the use of an endoscope deployed at the same time through the esophagus and into the stomach and maneuvered through he previously created anterior gastrostomy into the peritoneal cavity for diagnostic and therapeutic purposes.

Upon conclusion of such procedures, the physician may suture or staple all of the affected organs and the instruments may be withdrawn from the various ports 80, enabling the seals to return to fully closed positions, effectively sealing the outer end of the working channel 34. If another procedure is planned or is likely, the cannula 20 may remain in place. Alternatively, the cannula 20 may be removed and the opening 18 through the stomach peritoneum and skin may be closed by suturing, stapling or any other suitable method.

In one embodiment the anchor disc 70 will include a pre-positioned closure configuration as illustrated in FIG. 8. The anchor disc 70 includes opening on the external disc 400 for use with a needle catheter guide 402. The pre-positioned closure device allows for a suture 404 to be placed through the catheter and into the gastric lumen through the abdominal wall and gastric wall. A suture grasper is placed through a second catheter to aide in grasping the suture placed in another catheter. Consistent with the current state of the art the opening will be closed in a single or multiple layers. Repeating this process results in the pre-position of the closure sutures for use when the cannula 20 is removed.

Upon removal of the system 1 including cannula 20 the disc as illustrated in FIG. 8 is used to close the access to gastric lumen, peritoneal space, or retroperitoneal space.

The described transabdominal gastric surgery system and method provides for transabdominal gastric surgery access to the gastrointestinal tract and abdominal/pelvic cavity through multiple access ports at a variety of angles allowing triangulation and control of a plurality of instruments through a single surgical opening in a patient. Telescoping and expandable cannula may be employed to achieve dilation of the surgical opening or stoma. The system may also be employed to provide extralumenal access to the intestinal tract and other intrapertioneal organs.

As required, detailed embodiments of the transabdominal gastric surgical system and method have been disclosed herein. However, the disclosed embodiments are provided for illustration only and are merely exemplary of the [device/system/method], which may be embodied in various forms. Therefore, specific structural and functional details The following is claimed (and desired to be secured by Letters Patent):

1. A surgical system for providing transabdominal access for surgical instruments through a surgically constructed opening between an external body surface, the abdominal wall, and the stomach of a patient, the system comprising:
 a cannula including an inner end, an opposed outer end, and a sidewall extending between the ends, the sidewall circumscribing a lumen;
 an internal anchor assembly connected with the cannula adjacent the inner end, the internal anchor assembly being actuable between a nondeployed position to a deployed position disposed to contact the inner wall of the stomach;
 at least one external anchor for securing an outer portion of the cannula in place in the surgical opening adjacent the external surface, the external anchor selected from an array of anchor discs, each disc including an aperture sized for receiving the cannula therethrough;
 a cap including a plurality of access ports for introduction of surgical instruments through the cannula lumen and into the stomach of the patient, wherein each access port has an unique angular orientation relative to the cannula lumen to provide simultaneous transabdominal access to a plurality of surgical instruments at different angular orientations;
 a gas insufflation port connected to the cap for insufflation of a gas to the stomach to provide gastric distension;
 the access ports each including a double-seal disposed to reduce contamination of the cannula lumen and maintain intragastric insufflation by preventing escape of insufflated gas; and, the access ports configured to provide instrument access to the interior of the stomach of the patient at a plurality of different angles.

2. The system of claim 1, further including a closure demountably disposed adjacent the outer end of the cannula, the closure having an open position permitting access into the cannula lumen and a closed position blocking access into the cannula lumen.

3. The system of claim 1, wherein:
 a. the cannula includes a plurality of cannula sections, each section configured for telescoping reception of a portion of a lumen of an adjacent section so that the overall length of the cannula may be reduced during insertion;
 b. the sections being removably connected to permit removal of one or more sections from the end of the cannula.

4. The system of claim 3, wherein each cannula section is constructed of a material having different physical properties relative to another cannula section.

5. The system of claim 1, wherein the cannula includes a radially expandable sidewall configured to permit enlargement of the diameter of the cannula following insertion.

6. The system of claim 1, wherein the internal anchor assembly further comprises:
 a. a balloon element connected to an inflation tube, the inflation tube disposed to extend outside the external body surface of a patient;
 b. the inflation tube connected to an inflation valve; and
 c. the inflation valve being actuable to allow the passage of a liquid or gas through the inflation tube to inflate the balloon element from a deflated configuration to an inflated configuration within the stomach of a patient.

7. The system of claim 1, wherein:
 a. each anchor disc includes structure disposed to adjustably connect the disc to the cannula sidewall; and
 b. the anchor discs and internal anchor are disposed to cooperatively and adjustably create communication between the wall of the stomach to the abdominal wall of the patient.

8. A surgical system with a surgical system insertion tool for inserting a surgical system through a surgical opening and into the body of a patient and comprising:
 the surgical system of claim 1; and
 a surgical system insertion tool comprising:
  an elongate core element having a central lumen including a guide wire;
  the core having a first end and a second end, the first end configured to pass through the lumen of the cannula of the surgical system and entrain the cannula on the core;
  a tapered shield having a base end and an apertured tapered end, with a central lumen there between;
  the tapered shield configured to receive the core with entrained cannula for causing dilation of the surgical opening to receive the tool there through; and
  the tapered shield including at least one longitudinal score configured for tearing away the shield following placement of the cannula within the body of a patient;
 wherein the surgical system insertion tool is configured to connect to the surgical system for insertion of the surgical system through an external body surface, an abdominal wall, and a stomach of a patient.

9. The insertion tool of claim 8, wherein the tapered shield is configured disjoin from the introducer for removal, leaving the cannula in position.

10. The insertion tool of claim 8, wherein the insertion tool includes an inner bumper.

11. The insertion tool of claim 8, wherein the insertion tool is configured for communication and placement within a strippable PEG.

* * * * *